United States Patent [19]

Costantini et al.

[11] Patent Number: 5,159,120
[45] Date of Patent: Oct. 27, 1992

[54] PREPARATION OF DIALKOXYBUTENES

[75] Inventors: Michel Costantini; Dominique Laucher, both of Lyons, France

[73] Assignee: Rhone-Poulenc Chimie, Courbevoie, France

[21] Appl. No.: 714,584

[22] Filed: Jun. 13, 1991

[30] Foreign Application Priority Data

Jun. 13, 1990 [FR] France .................................. 90 07608

[51] Int. Cl.$^5$ .............................................. C07C 41/01
[52] U.S. Cl. .................................... 568/673; 568/674; 568/660
[58] Field of Search ........................ 568/660, 673, 674

[56] References Cited

U.S. PATENT DOCUMENTS 4,533,761 8/1985 Peterson .
4,843,180 6/1989 Mullins .

FOREIGN PATENT DOCUMENTS 1138366 1/1969 United Kingdom .

Primary Examiner—Marianne M. Cintins
Assistant Examiner—John Peabody
Attorney, Agent, or Firm—Burns, Doane, Swecker & Mathis

[57] ABSTRACT

Dialkoxybutenes are selectively prepared in high yields by reacting 1,3-butadiene with an alcohol in the presence of oxygen and a catalytically effective amount of solid particulates which comprise a catalytically active phase deposited onto particles of a support therefor, such catalytically active phase comprising at least one Group VIII noble metal first component, at least one tellurium, selenium and/or sulfur second component, and, optionally, at least one bismuth, antimony, copper and/or tin third component.

19 Claims, No Drawings

PREPARATION OF DIALKOXYBUTENES

BACKGROUND OF THE INVENTION

1. Field of the Invention

The present invention relates to the preparation of dialkoxybutenes, and, more especially, to the selective preparation of dialkoxybutenes by reacting 1,3-butadiene with an alcohol in the presence of oxygen and particular composite catalyst.

2. Description of the Prior Art

GB-A-1,138,366 describes the preparation of 1,4-dimethoxy-2-butene by reacting 1,3-butadiene with methanol in the presence of a solution of palladous chloride and cupric chloride dihydrate. It also suggests that reactions of this type be conducted in liquid phase in the presence of salts other than nitrates and sulfates or of coordination compounds of palladium, platinum, nickel, iron or cobalt and of an inorganic redox system. However, the efficiency of this process remains low in homogeneous phase; the yield of dimethoxybutenes is insufficient and a significant amount of byproducts is obtained.

U.S. Pat. No. 4,533,761 describes the preparation of dialkoxybutenes by reacting 1,3-butadiene with an alkanol, the alkanol constituting the reaction medium, in the presence of iodide and copper ions.

However, this reaction appears to be stoichiometric relative to the copper and the undesired formation of various byproducts is again observed.

SUMMARY OF THE INVENTION

Accordingly, a major object of the present invention is the provision of an improved process for the preparation of dialkoxybutenes from 1,3-butadiene and an alcohol, which improved process avoids or conspicuously ameliorates the above disadvantages and drawbacks to date characterizing the state of this art.

Briefly, the present invention features a process for the preparation of dialkoxybutenes by reacting 1,3-butadiene with an alcohol in the presence of oxygen and a catalyst, said catalyst comprising a solid including at least one first component selected from among the noble metals of Group VIII of the Periodic Table of the elements and at least one second component selected from among tellurium, selenium and sulfur, said at least one first and second components being deposited, e.g., onto suitable support particulates.

DETAILED DESCRIPTION OF THE PREFERRED EMBODIMENTS OF THE INVENTION

More particularly according to the present invention, it is known to this art that the dialkoxybutenes are useful intermediates, especially for the preparation of furan compounds. As utilized herein, by the term "dialkoxybutenes" are intended 1,4-dialkoxy-2-butenes and 1,2-dialkoxy-3-butenes, the linear, branched or cyclic alkoxy moieties of which contain from 1 to 12 carbon atoms and, preferably, from 1 to 5 carbon atoms. These diethers can be prepared according to the invention by reacting 1,3-butadiene with an alcohol, and said alcohol can itself constitute the reaction medium. A linear, branched or cyclic alcohol having from 1 to 12 carbon atoms and, preferably, from 1 to 4 carbon atoms, is advantageously employed. Such alcohol and the 1,3-butadiene may be of technical grade.

Exemplary alcohols for carrying out the process of the invention include methanol, ethanol, isopropanol, tert-butanol, benzyl alcohol, 2-phenylethanol and trifluoroethanol. Methanol and ethanol are more particularly preferred.

According to the present invention, a solid catalyst is employed, comprising at least one first component selected from among the noble metals of Group VIII of the Periodic Table and at least one second component selected from among tellurium, selenium and sulfur; these components are deposited onto suitable support particulates.

Exemplary first components of the catalyst comprise, more particularly, palladium, rhodium or platinum and, advantageously, palladium-based catalysts are used.

The support employed for the catalyst preparation is not critical. Exemplary such supports include, especially, active carbons, silica gels, silica-alumina mixtures, alumina, clays, bauxite, magnesia, diatomaceous earth, etc.

The active carbons are advantageously used to satisfactorily carry out the process of the present invention.

The amount of component(s) selected from among the noble metals of Group VIII can vary over wide limits. For economic reasons, a maximum concentration of such an element on the support on the order of 20% by weight of the solid catalyst is used, although higher amounts are not precluded.

To attain an acceptable reaction rate, it is preferable that this concentration be at least 0.1% by weight.

In a preferred embodiment of the invention, the solid catalyst also comprises at least one additional third component selected from among bismuth, antimony, copper and tin.

Although the amount of such additional components on the support, as in the case of the second component(s), can vary over wide limits, such amount advantageously ranged from 0.03% to 30% by weight of the catalyst.

Tellurium is the preferred second component. The tellurium may be present either alone or in combination with at least one of the additional elements selected from among copper, tin and antimony.

The molar ratio between each of the second or additional elements and the noble metal(s) of Group VIII advantageously ranges from 0.01 to 10 and preferably from 0.1 to 5.

Good results are attained using a palladium/tellurium pair, or couple, in the mentioned molar ratios, the same being deposited onto active carbon and, if appropriate, in combination with copper, tin or antimony.

Conventional techniques per se known to the art for preparing supported metal catalysts may be employed to prepare the supported catalyst that is used to carry out the process of the present invention.

For example, the catalyst may be prepared by introducing a support into a solution which is prepared by dissolving at least one appropriate compound of the selected element(s); the deposition of the active component(s) onto the support is carried out by distilling off the solvent and the mass thus obtained is reduced by means of a stream of hydrogen, or with a reducing compound such as hydrazine, methanol and formalin.

According to another conventional method of preparation, the deposition of the active component(s) onto the support is carried out by precipitating the compounds in known manner and also subjecting the mass thus obtained to a reduction.

Other methods of preparation are also possible, in particular the impregnation of a support with a solution of the appropriate compound(s) in the presence of an organic agent such as hydrazine.

The deposition of a plurality of components onto the support can, of course, be carried out simultaneously or separately.

The nature of the compound of at least one noble metal of Group VIII which is employed for the preparation of the catalyst according to the present invention is not critical. Similarly, the precise nature of the compound(s) of the other elements is also not critical.

If desired, the metals themselves may be employed, such as metallic palladium, metallic rhodium, metallic tellurium, metallic bismuth and metallic copper.

Exemplary compounds used for the preparation of the catalysts include palladium chloride, platinum chloride, palladium acetate, platinum acetate, mixed sodium palladium chloride, mixed sodium palladium sulfate, hexachloroplatinic acid, rhodium nitrate, antimony chloride, bismuth chloride, tellurium (II) or (IV) chloride, selenium(II) or (IV) chloride, tellurium (IV) or (VI) oxide, selenium oxide, copper acetate, antimony acetate, bismuth nitrate and bismuth chloride.

The particle size of the catalyst/support particulates typically ranges from 0.1 to 10 mm, it being appreciated that larger or smaller sizes may be selected. The size which is actually selected depends, as is known to this art, on the particular parameters of the forming process.

As indicated above, the dialkoxybutenes are prepared by reacting 1,3-butadiene with an alcohol in the presence of a solid catalyst, as described above, and also in the presence of oxygen.

The reaction is advantageously carried out in the liquid phase, by suspending the solid catalyst in the reaction medium comprising an alcohol and by injecting 1,3-butadiene and a gas containing molecular oxygen therein. Such gas may be pure oxygen or oxygen diluted with an inert gas, for example air. The amount of oxygen is of critical nature only insofar as it must be such that neither the feed gases nor any gas phase which may be created in the reaction zone is within the explosive composition range, considering the other parameters or reaction conditions selected. The amount of oxygen in relation to the butadiene may be in excess or in deficiency relative to the stoichiometry of the reaction.

The amount of noble metal of Group VIII of the Periodic Table may vary over wide limits relative to the butadiene. This amount (on a molar basis) typically ranges from $10^{-5}$ to $10^{-2}$ and preferably from $10^{-4}$ to $10^{-3}$.

The partial pressure of the oxygen, measured at 25° C., preferably ranges from 0.1 to 20 bar.

The reaction temperature typically ranges from 20° to 160° C. and preferably from 70° to 120° C. Below 70° C. the reaction rate is relatively slow and above 120° C. a decomposition of the reactants and of the reaction products can be observed.

Depending upon the particular operating technique, the reaction pressure typically ranges from atmospheric pressure to approximately 300 bar. A pressure ranging from 1 to 100 bar is preferred.

Upon completion of the reaction or after lapse of that period of time allocated thereto, the required dialkoxybutenes are recovered by any suitable means, for example by distillation and/or extraction, if appropriate after filtration or decanting from the solid catalyst.

In order to further illustrate the present invention and the advantages thereof, the following specific examples are given, it being understood that same are intended only as illustrative and in nowise limitative.

EXAMPLE 1

(a) Treatment of the Carbon Employed as the Catalyst Support

Active carbon supplied by CECA S.A., of 3S type and having a BET surface area of 1,150 m$^2$/g (100 g) was suspended in a 30% strength aqueous solution of nitric acid (600 ml). The mixture was refluxed for 2 hours. The aqueous solution was removed by filtration and the carbon was washed with demineralized water until a pH of 4 was attained in the wash water. The carbon was dried at 90° C. at a reduced pressure of 20 mm Hg.

(b) Preparation of the Catalyst Containing Palladium and Tellurium

The carbon (10 g) thus treated was suspended in a 30% strength aqueous solution of nitric acid (40 ml) in which palladium acetate (2 mmol, 448 mg) and tellurium dioxide (0.6 mmol; 160 mg) had been dissolved. The solvent was removed by distillation in a rotary evaporator at reduced pressure. The solids thus obtained were dried at 80° C. at reduced pressure (20 mm Hg).

The catalyst was reduced for 2 hours at 200° C. and 2 hours at 400° C. with a stream of methanol-saturated nitrogen (60 l/h) containing 2% of oxygen for 16 hours at 300° C. and was again reduced with a stream of methanol-saturated nitrogen for 2 hours at 200° C. and 2 hours at 400° C.

(c) Methoxylation

The catalyst (1 g) thus prepared was charged with methanol (30 ml) and butadiene (80 mmol; 4.3 g) into a tantalum autoclave of 120 ml internal capacity, stirred by shaking. The autoclave was pressurized to 100 bar with air containing 21% of O$_2$ and was then heated to 90° C. for 12 hours. The autoclave was cooled and then degassed and the contents were determined by gas phase chromatography. 7.7 mmol of 1,2-dimethoxy-3-butene (1,2-DMBE) and 23 mmol of cis + trans 1,4-dimethoxy-2-butene (1,4-DMBE) were obtained.

EXAMPLE 2

The procedure of Example 1 was repeated, but the reaction was carried out for 23 hours. 10.2 mmol of 1,2-DMBE and 30.2 mmol of cis + trans 1,4-DMBE were obtained.

EXAMPLE 3

The catalyst was prepared according to the procedure of Example No. 1, but using 50S carbon (supplied by CECA S. A., having a BET surface area of 1500 mm$^2$/g). This catalyst was employed in the methoxylation reaction described in Example 1. 4 mmol of 1,2-DMBE and 8.5 mmol of cis + trans 1,4-DMBE were obtained.

EXAMPLE 4

Catalyst Containing Pd/Te/Cu

The catalyst was prepared as in Example 1, except that 4.8 mmol of palladium acetate, 0.4 mmol of tellurium dioxide and 13.4 mmol of copper acetate were dissolved in the 30% strength aqueous solution of nitric acid. The methoxylation was carried out in the same manner as in Example 1. 2 mmol of 1,3-DMBE and 0.2 mmol of 1,4-DMBE were obtained.

EXAMPLE 5

Catalyst Containing Pd/Te/Sn

The catalyst was prepared as in Example 1, except that 0.7 mmol of palladium acetate, 0.25 mmol of tellurium dioxide and 0.62 mmol of stannous chloride were dissolved in the 30% strength aqueous solution of nitric acid. The methoxylation was carried out in the same manner as in Example 2. 1.1 mmol of 1,3-DMBE and 2.4 mmol of 1,4-DMBE were obtained.

EXAMPLE 6

Catalyst Containing Pd/Te/Sb

The catalyst was prepared as in Example 1, except that 2 mmol of palladium acetate, 0.7 mmol of tellurium dioxide and 1.94 mmol of antimony acetate were dissolved in the 30% strength aqueous solution of nitric acid. The methoxylation was carried out in the same manner as in Example 2. 13.2 mmol of 1,2-DMBE and 30.3 mmol of 1,4-DMBE were obtained.

EXAMPLE 7

Catalyst (1 g) prepared according to the procedure described in Example 6, methanol (30 mml) and butadiene (35 mmol; 1.89 g) were charged into a 120-ml autoclave stirred by shaking. The autoclave was pressurized to 80 kg/cm$^2$ with air containing 21% of oxygen and was heated to 90° C. for twelve hours. The autoclave was cooled and then degassed and the contents were determined by gas phase chromatography. 9.3 mmol of 1,3-DMBE and 20 mmol of cis + trans 1,4-DMBE were obtained.

EXAMPLE 8

A reaction was carried out using the catalyst and according to the procedure described in example 6, except that the methanol was replaced with an equivalent amount of 2-propanol (30 ml). 1.8 mmol of 1,3-diisopropoxy-3-butene and 9.7 mmol of cis + trans 1,4-diisopropoxy-2-butene were obtained.

EXAMPLE 9

A reaction was carried out using the catalyst and according to the procedure described in Example 6, except that the methanol was replaced with an equivalent amount of 2-methylpropanol. 0.4 mmol of trans-1,4-di(2-methyl-2-propoxy)-2-butene were obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a dialkoxybutene, comprising reacting 1,3-butadiene with an alcohol in the presence of oxygen and a catalytically effective amount of solid particulates which comprise a catalytically active phase deposited onto particles of a support therefor, said catalytically active phase comprising at least one Group VIII noble metal first component and at least one tellurium, selenium or sulfur second component.

2. The process as defined by claim 1, the first component of said catalytically active phase comprising palladium, platinum or rhodium.

3. The process as defined by claim 2, the first component of said catalytically active phase comprising palladium.

4. The process as defined by claim 1, said catalytically active phase further comprising at least one bismuth, antimony, copper or tin third component.

5. The process as defined by claim 1, the second component of said catalytically active phase comprising tellurium.

6. The process as defined by claim 5, said catalytically active phase further comprising at least one copper, antimony or tin third component.

7. The process as defined by claim 1, said support particles comprising active carbon.

8. The process as defined by claim 1, said solid particulates comprising from 0.01% to 20% by weight of said Group VIII noble metal first component.

9. The process as defined by claim 4, said solid particulates comprising from 0.01% to 30% by total weight of said second and said third components.

10. The process as defined by claim 1, wherein the molar ratio between said second component and said Group VIII noble metal first component ranges from 0.01 to 10.

11. The process as defined by claim 10, said molar ratio ranging from 0.1 to 5.

12. The process as defined by claim 4, wherein the molar ratio between said third component and said Group VIII noble metal first component ranges from 0.01 to 10.

13. The process as defined by claim 12, said molar ratio ranging from 0.1 to 5.

14. The process as defined by claim 1, carried out at a temperature ranging from 20° to 160° C.

15. The process as defined by claim 14, carried out at a temperature ranging from 70° to 120° C.

16. The process as defined by claim 1, wherein the partial pressure of said oxygen, measured at 25° C., ranges from 0.1 to 20 bar.

17. The process as defined by claim 1, carried out in liquid phase.

18. The process as defined by claim 1, said alcohol comprising a linear, branched or cyclic alcohol having from 1 to 12 carbon atoms.

19. The process as defined by claim 18, said alcohol comprising methanol or ethanol.

* * * * *